US008649015B2

(12) United States Patent
Ichihara et al.

(10) Patent No.: US 8,649,015 B2
(45) Date of Patent: Feb. 11, 2014

(54) BIOINFORMATION ACQUISITION APPARATUS

(75) Inventors: Shigeru Ichihara, Tokyo (JP); Shuichi Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 276 days.

(21) Appl. No.: 12/900,869

(22) Filed: Oct. 8, 2010

(65) Prior Publication Data

US 2011/0102797 A1    May 5, 2011

(30) Foreign Application Priority Data

Nov. 4, 2009 (JP) ................................. 2009-253047

(51) Int. Cl.
G01N 21/00 (2006.01)
G01N 21/55 (2006.01)

(52) U.S. Cl.
USPC .......................................... 356/445; 356/432

(58) Field of Classification Search
USPC ................... 356/445–448, 450–458
See application file for complete search history.

(56) References Cited

U.S. PATENT DOCUMENTS

| | | | | |
|---|---|---|---|---|
| 5,077,803 A | * | 12/1991 | Kato et al. | 382/124 |
| 5,550,798 A | * | 8/1996 | Hineno et al. | 369/110.04 |
| 6,002,499 A | * | 12/1999 | Corboline et al. | 359/2 |
| 6,032,070 A | * | 2/2000 | Flock et al. | 600/473 |
| 6,885,808 B2 | * | 4/2005 | Hatakoshi | 385/146 |
| 7,006,861 B2 | * | 2/2006 | Flock et al. | 600/473 |
| 7,308,123 B2 | * | 12/2007 | Fenrich et al. | 382/125 |
| 7,397,570 B2 | * | 7/2008 | Kawasaki et al. | 356/512 |
| 7,539,330 B2 | * | 5/2009 | Rowe | 382/124 |
| 8,229,185 B2 | * | 7/2012 | Ennis et al. | 382/124 |
| 8,244,006 B2 | * | 8/2012 | Yokoyama et al. | 382/124 |
| 2006/0184042 A1 | | 8/2006 | Wang et al. | 600/476 |
| 2008/0285812 A1 | * | 11/2008 | Rensen et al. | 382/115 |
| 2009/0243610 A1 | | 10/2009 | Ichihara et al. | 324/301 |
| 2010/0058870 A1 | | 3/2010 | Kobayashi | 73/596 |
| 2010/0164906 A1 | * | 7/2010 | Fukunaga et al. | 345/175 |
| 2010/0319453 A1 | | 12/2010 | Ichihara et al. | 73/596 |

FOREIGN PATENT DOCUMENTS

| | | |
|---|---|---|
| JP | 62-130650 U | 8/1987 |
| JP | 2009-031268 A | 2/2009 |
| JP | 2009-136321 A | 6/2009 |

OTHER PUBLICATIONS

D. Razansky et al., "Polarization-Sensitive Pptoacoustic Tomography of Optically Diffuse Tissues" Optics Letters, vol. 33, No. 20, pp. 2308-2310 (2008).

* cited by examiner

Primary Examiner — Kara E Geisel
Assistant Examiner — Jarreas C Underwood
(74) Attorney, Agent, or Firm — Fitzpatrick, Cella, Harper & Scinto

(57) ABSTRACT

In a bioinformation acquisition apparatus, a flux of light emitted from a test object through diffusion when the test object is irradiated with light can be reused, improving use efficiency of the radiated light. The apparatus has a light source for irradiating the test object with the flux of light, and a detector for detecting a signal output based on the radiation, and includes: a reflection-type polarization element adapted that at least a part of the flux of light from the light source can be transmitted through, and a flux of light emitted from the test object by the radiation can be reflected, in which the reflection-type polarization element is disposed at a position opposite to an irradiation area of the light on the surface of the test object to cover the irradiation area.

14 Claims, 6 Drawing Sheets

BIOINFORMATION ACQUISITION APPARATUS

BACKGROUND OF THE INVENTION

1. Field of the Invention

The present invention relates to a bioinformation acquisition apparatus using light and in particular to technology for enhancing optical energy use efficiency by re-irradiating a living body with a flux of light that has diffused through and been emitted from a living body.

2. Description of the Related Art

Research and development have been done for visualizing information in a living body by using near infrared rays because infrared light is noninvasive and is transmitted well through a living body, i.e., a test object. In vivo material such as water, fat or hemoglobin present in a blood vessel has a peculiar spectrum in the near-infrared wavelength range. Much study, therefore, has directed to visualizing a spatial coefficient distribution of absorption originating from those components to acquire functional information in a living body.

A method for detecting optical absorption in a living body includes diffuse measurement (DOT: Diffuse Optical Tomography), in which a flux of light that has been transmitted through a living body is directly measured, and photoacoustic measurement (PAT: Photo Acoustic Tomography), using the photoacoustic effect.

In PAT, a living body is irradiated with pulsed light generated by a light source, and an acoustical wave, produced when the living body absorbs optical energy from the pulsed light which propagates and is diffused therein, is measured. That is, an elastic wave produced when a test site expands instantaneously by absorbing radiated optical energy is received by a transducer, taking advantage of a difference in absorption coefficient of optical energy between the test site such as a tumor and tissue other than the test site. This detection signal can be analyzed and processed, providing an optical characteristics distribution in a living body, particularly an optical energy absorption density distribution. An ultrasonic wave has high straightness in a living body compared with light, and hence can be observed with a high spatial resolution by using a photoacoustic measurement apparatus for detecting ultrasonic waves.

U.S. Patent Application Publication No. 2006/0184042 proposes an apparatus as a bioinformation imaging apparatus using the photoacoustic effect. The apparatus disclosed in that document is adapted so that light radiated to a desired area in a living body is collected by a lens having a light-collecting function, and a photoacoustic signal is detected, while making efficient use of optical energy.

SUMMARY OF THE INVENTION

The bioinformation imaging apparatus of a conventional example described above using photoacoustic effect can acquire a stronger acoustical wave signal by applying a large amount of optical energy to a living body.

However, using such photoacoustic effect has a problem in that an acoustical wave signal coming from a deep portion in a living body has a lowered strength, because the optical energy of the flux of light that has reached that deep portion has been attenuated. Therefore, it is necessary to use a pulsed light source generator having high power as a light source to observe a deep portion of a living body, but the pulsed light source generator is limited in output and furthermore such a pulsed light source generator is expensive. Further, there also arises a problem that as the output is made higher, it becomes unstable.

Therefore, to enhance observation capability in a deep portion of a living body, it is desirable to use optical energy more efficiently.

One method by which optical energy use efficiency is expected to be enhanced is to reuse backscattering light that is a flux of light emitted from a living body through the effect of diffusion in the living body.

That is, a flux of light radiated into a living body loses straightness due to strong diffusion in the living body, and a part of the light flux is radiated from an irradiation area and adjacent areas outside the body due to backscattering. By reusing this emitted flux, it can be expected to enhance the strength of a signal.

On the one hand, in an approach disclosed in U.S. Patent Application Publication No. 2006/0184042, as described above, it is proposed to collect light in a desired area of a living body by using a lens having a light-collecting function. According to such an approach, a flux of light can be directly radiated into a living body to enhance optical energy use efficiency, but this approach cannot efficiently function so as to reuse the backscattering light described above.

An objective of the present invention, in terms of the aforementioned problems, is to provide a bioinformation acquisition apparatus which can reuse a flux of light emitted from a test object due to diffusion in the test object when the test object is irradiated with light, and can enhance use efficiency of the radiated light.

The present invention provides a bioinformation acquisition apparatus adapted in the following manner.

The bioinformation acquisition apparatus according to the present invention having a light source for irradiating a test object with a light flux, and a detector for detecting a signal output based on radiation of the light flux to the test object, includes a reflection-type polarization element adapted so that at least a part of the flux of light coming from the light source can be transmitted through, and a flux of light emitted from the test object by the radiation of the flux of light to the test object can be reflected, in which the reflection-type polarization element is disposed at a position opposite to an irradiation area of the flux of light on the surface of the test object to cover the irradiation area.

According to the present invention, a flux of light emitted from a test object when the test object is irradiated with light is reflected by a reflection-type polarization element and projected to the test object again, so that the flux of light emitted from the test object can be reused, improving use efficiency of the radiated light.

Further features of the present invention will become apparent from the following description of embodiments with reference to the attached drawings.

DESCRIPTION OF THE EMBODIMENTS

Figure 1:
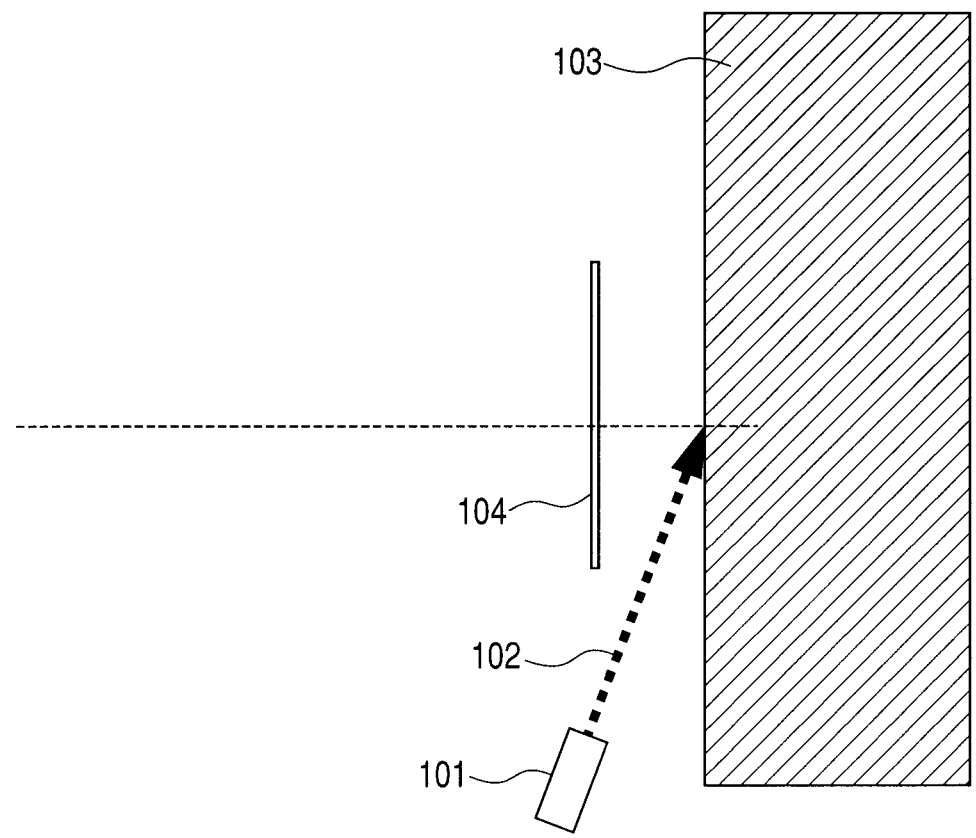
FIG. 1 illustrates a model for measuring a backscattering distribution to confirm a distribution of light that is backscattered and emitted.

Preferred embodiments of the present invention will now be described in detail in accordance with the accompanying drawings.

A bioinformation acquisition apparatus in an embodiment of the present invention will be described.

The bioinformation acquisition apparatus according to the present embodiment includes a light source for irradiating a living body (i.e., a test object) with a flux of light, a detector for detecting a signal output based on the irradiation of the body with the light flux by the light source, and a reflection-type polarization element for reflecting a flux of light emitted from the living body.

A signal provided by the detector described above can be processed to measure a variety of biological information. In doing so, the flux of light emitted from the living body when the body is irradiated with light can be reflected by a reflective member that is the reflection-type polarization element described above to be projected to the living body again, improving use efficiency of the radiated light.

The detector used here may include an ultrasonic detector used for detecting an acoustical wave signal in photoacoustic measurement, and a light detector used for detecting a modulated optical signal provided by radiating an ultrasonic signal to a living body in ultrasonic optical modulation signal measurement.

PAT measurement can be carried out when an acoustical wave-detector is provided as a detector to detect, as "a signal output based on radiation of a flux of light to a living body", an acoustical wave produced in a local area inside a test object due to irradiation of pulsed light. On the other hand, Diffuse Optical Tomography (DOT) measurement, Acousto-Optical Tomography (AOT) measurement and the like can be carried out when a light detector is provided to detect, as "a signal output based on radiation of a flux of light to a living body", weak light which has propagated and been diffused inside a living body, or light modulated by an ultrasonic wave.

DOT is the technology by which light from a light source is directed to a living body, weak light which has propagated and been diffused inside the living body is sensed by a highsensitive light detector, and an optical characteristic values distribution inside the living body is imaged from a sensed signal.

In AOT, light is radiated into living tissue, and at the same time an ultrasonic wave converged onto a local area is radiated thereinto, and modulated light is detected by a light detector by using an effect in which light is modulated by an ultrasonic wave (acousto-optical effect). Also, AOT can detect X-ray phase variation in living tissue corresponding to absorption of optical energy.

In this specification, photoacoustic measurement using an acoustical wave-detector will be mainly described, but the present invention, needless to say, can apply to various bioinformation acquisition apparatuses in which optical energy is required to be used efficiently.

A pulsed laser is mainly used as the light source for the photoacoustic measurement apparatus.

When a laser is used as the light source, maximum permissible exposure (MPE) that is irradiation energy per unit area permitted to be applied to the surface of a living body is provided by the International Code of laser usage. On the other hand, as stronger optical energy is applied to a living body, a stronger acoustical wave signal can be provided. Therefore, a wide area can be illuminated with permissible light exposure to radiate a large amount of optical energy.

A flux of light radiated into a living body is more strongly diffused by cellular tissues and the like inside the living body and loses straightness, and a part thereof is backscattered and emitted from the living body.

When a flux of light is applied to a uniform diffuse material having equivalent optical characteristics to a living body, most of the light flux that is backscattered due to diffusion is emitted from the living body.

These events are analyzed by using a model shown in FIG. 1 through Monte Carlo simulation which is a ray tracing approach, to confirm a distribution of diffuse light to be emitted. A flux of light 102 having the diameter of 5 mm emitted from a light source 101 is obliquely projected into a uniform diffuse material 103 having an equivalent optical constant as a living body, and a distribution of diffused light is observed on the detection surface 104 disposed in front of an irradiation area. An emitted flux of light has a distribution in which a large amount of light lies directly on the irradiation area irrespective of an incident angle and irradiates the detection surface at a certain spread angle. That is, the flux of light projected into the living body is diffused inside the living body and emitted from the living body in a range equal to or greater than the radiation area at an adequate angle centered on and spread around the vertical direction.

Hereinafter, the diffuse light emitted from a living body in such a manner will be called "emitted and diffused light".

To re-illuminate the inside of a living body with emitted and diffused light, a reflective member using a mirror for reflection may be also used, but a reflection-type polarization element can be used to provide the following advantages in the present invention.

Use of the reflection-type polarization element can allow a linear polarization component of emitted and diffused light, different from the reflection-type polarization element described above, to be selectively reflected and re-radiated. If the reflection-type polarization element reflects an s-polarization component, the reflection-type polarization element reflects an s-polarization component of the emitted and diffused light with which a living body is re-illuminated. Differing from a reflective member such as a mirror, a reflection function of the reflection-type polarization element depends on a polarization state of the emitted and diffused light.

In addition, the -type polarization element can be disposed at a position at which an ordinary reflective member such as a mirror cannot be disposed. The reflection-type polarization element, to transmit a flux of light having the same linear polarization component without loss, can be disposed in a propagation path of the flux of light, including being disposed in contact with an irradiation area on the surface of a living body. That is, if polarization of light radiated from a light source corresponds with polarization of light which the reflection-type polarization element transmits, there can be many degrees of freedom for positioning a polarization element. In the case of contact positioning of the reflection-type polarization element, an irradiation area to which a flux of light is first radiated can be efficiently re-illuminated with the emitted and diffused light. On the other hand, as described above, the emitted and diffused light is emitted outside and spread from the surface of a living body, so that if using a mirror, it is necessary to consider a size and positioning to receive the flux of light of the emitted and diffused light entirely.

Also, if the reflection-type polarization element is used, a desired area can be efficiently illuminated with the necessary amount of light irrespective of the diffuse direction.

Also, use of the reflection-type polarization element has an advantage that it is easy to illuminate the surface of a living body approximately vertically thereto, which advantage a reflective member such as a mirror does not have (the term "approximately vertically" will be used here instead of the term "vertically" because the surface of a living body is not completely flat). Radiating the flux of light approximately vertically can allow optical energy stronger than oblique radiation to be imparted to a deep portion of a living body and can function in an effective manner.

On the other hand, the reflection-type polarization element has a drawback that a polarization component in the same direction is not reflected and the polarization component is transmitted through the element, so that the polarization component cannot be reused. If light having a polarization component which is transmitted through the -type polarization element is applied to a living body, light rays of the radiated light are repeatedly scattered inside the living body and lose directionality, and thus a part of backscattering light is not transmitted through the reflection-type polarization element. However, as described in detail later, not all the light acts in this fashion.

As aforementioned, although in some case the reflection-type polarization element may have a lower effectiveness, as compared with use of an ordinary reflective member such as a mirror, the reflection-type polarization element can be used with a mirror, as will be described later, and more efficiently re-illuminate a living body with the emitted and diffused light.

The reflection-type polarization element may be sized and disposed enough to cover a propagating area of the emitted and diffused light.

When the reflection-type polarization element is positioned in contact with a living body, the size of the reflection-type polarization element can be equal to or larger than an irradiation area to entirely cover an area where the emitted and diffused light is emitted. When the reflection-type polarization element is contactlessly positioned, a reflection-type polarization element further larger than that positioned in contact with the living body can be positioned near the living body above the irradiation area in the direction normal thereto.

However, it is more effective to position a reflective member such as a mirror rather than the reflection-type polarization element in a place other than a path through which the flux of light emitted from the light source propagates.

Here, polarization characteristics will be briefly described.

In the present invention, polarization characteristics of a flux of light are used. A polarization state may be divided into classes of linear polarization, circular polarization and elliptical polarization, based on the shape of an electric field vector locus of the light flux passing through.

Unpolarized light such as that which results from incandescence has all of the polarization states, i.e., linear polarization, circular polarization and elliptical polarization, overlapping with each other. On the other hand, randomly polarized light such as laser light has polarization planes that are orthogonal to each other, and in the output of each polarization component are two linearly polarized collimated beams that randomly and temporally change overlap with each other.

The photoacoustic measurement apparatus needs strong optical energy to acquire biological information, and flashlamp-pumped pulsed laser is mainly used as the light source. In such a pulsed laser, linearly polarized laser light having a certain polarization plane is emitted.

Therefore, in the present invention, a living body can be illuminated with a flux of light without loss of optical energy by positioning a reflection-type polarization element to transmit a polarization component in the same direction as that of the light source.

The reflection-type polarization element is constructed by laminating a dielectric thin film having a thickness of a half wavelength. When a polarization component of a light source and that of a polarization element have the same direction the polarization component of the light from the light source can be transmitted without reflection loss, but when those polarization components have different directions from each other, the polarization component of the light from the light source is reflected. A polarization beam splitter using polarization characteristics takes advantage of this fact, and on one surface of oblique sides of one of a prism used, a dielectric thin film having the thickness of a half wavelength is coated by a multilayer lamination method.

Further, a wire grid polarizer in which thin metal wires are arrayed regularly parallel to each other on a substrate such as glass can be also used. Incident light including a p-polarization component and an s-polarization component is divided into p-polarized light and s-polarized light due to birefringent effect on the wire grid surface formed of an aluminum wire net. The incident light hits against the wire grid surface, the p-polarization component, then enters and is transmitted through a portion of the dielectric material, but the s-polarization component is reflected.

The research on photoacoustic effect dependent on polarization characteristics of living tissue has been reported by Daniel Razansky et al., under the title "Polarization-Sensitive Optoacoustic Tomography of Optically Diffuse Tissues", in *Optics Letters*, Vol. 33, No. 20, pp. 2308-2310.

Razansky et al. do not have the concept of re-illumination with the emitted and diffused light, and aim to quantitatively evaluate strength of a photoacoustic signal produced from a polarization member disposed inside a simulated living body, based on a polarization state of a flux of light radiated to a living body.

In this research, to control a polarization state of the flux of light, a polarization element is used, but the features of the polarization element are not described. If a reflection-type polarization element is used as a member for controlling polarization, it would be expected that the quantitativeness of the experiment might be spoiled due to reflection of emitted and scattered light, but the result of the experiment seems not to be affected by the emitted and scattered light. Therefore, it can be inferred that the research does not use a reflection-type polarization element and thus does not connect with the present invention.

However, this research shows that a polarization state of a flux of light radiated to a diffuse medium which is a simulated living body is also maintained to some degree inside a living body. The polarization state of emitted and diffused light travelling in the direction opposite to the incident direction is not precisely understood, but it is guessed that a part of the polarization state of the incident light is maintained in the emitted and diffused light.

For example, when a p-polarized flux of light is transmitted through a reflection-type polarization element to be radiated to the surface of a living body, emitted and diffused light maintaining a p-polarization state is not reflected by a polarization element and it is transmitted therethrough, resulting in poor efficiency.

In such a case, a λ/4 wave plate can be inserted between the living body and the reflection-type polarization element to improve efficiency. Generally, a p-polarization state of a flux of light which has passed through a polarization element forms circular polarization due to the λ/4 wave plate. If this flux of light is regularly reflected, its polarization state is transformed from circular polarization to linear polarization of s-polarization when the flux of light passes through the λ/4 wave plate again.

Here, if emitted and diffused light having pseudo-circularly polarized light on which the effect of a p-polarization component remains passes through the λ/4 wave plate again rather than the flux of light regularly reflected, then the polarization state of the flux of light forms pseudo-linear polarization on which the effect of an s-polarization component remains. Thus, the emitted and diffused light will be efficiently reflected by the reflection type polarization element. By using the λ/4 wave plate depending on the polarization state of the emitted and diffused light, the amount of light reflected by the reflection-type polarization element can be increased.

In a bioinformation measurement apparatus using photoacoustic effect, measurement apparatuses are proposed which have different positions of an illumination position and an ultrasonic detector relative to a living body which is a test object. That is, there may be cases where the ultrasonic detector is positioned opposite to the illumination position relative to a living body, or the ultrasonic detector is disposed on the side of an illumination area.

Particularly in the case where the ultrasonic detector is disposed on the side of the illumination area, a flux of light can be applied to the surface of a living body facing the ultrasonic detector disposed near the living body. In the case of such an arrangement, the emitted and diffused light travels toward the front of the ultrasonic detector, so that the reflection-type polarization element can be positioned between the ultrasonic detector and the irradiation surface. In doing so, it is necessary for the reflection-type polarization element to also have capability for transmitting an acoustical wave signal.

A reflection-type polarization element that transmits an acoustical wave is a member in which the acoustical wave transmitted therethrough may be attenuated in very small measure. Such a member is formed of a material having a small attenuation rate of acoustical waves, or a material which easily attenuates an acoustical wave but has its thickness sufficiently small compared to the wavelength of an acoustical wave, that it is capable of transmitting an acoustical wave.

The reflection-type polarization element uses a thin film in which dielectric films having the thickness of approximately a half wavelength are coated in thickness of several μm on a substrate material by a multilayer lamination method, so that the capability for transmitting an acoustical wave can be maintained. Also, a member such as polymethylpentene having a relatively good capability for transmitting an acoustical wave can be used as a substrate material, resulting in minimum attenuation of an acoustical wave.

When an ultrasonic wave is detected, a material for acoustically matching an ultrasonic detector to a living tissue is provided, and in contact with the material, a reflection-type polarization element is positioned. Here, acoustic impedance of the living tissue has a value near that of water, i.e., $1.5 \times 10^6$ $kg \cdot m^{-2} \cdot s$, and the impedance is about $1500 \ m \cdot s^{-1}$ at the velocity of sound.

The frequency of an ultrasonic detector used in the present invention is in the range of about 1-50 MHz, and the computed length of one wavelength is in the range of about 1.5 mm-30 μm.

A sufficiently thinner film thickness of the reflection-type polarization element can allow the capability for transmitting an acoustical wave to be enhanced independent of an element material. When an acoustical wave signal having the frequency of 5 MHz is temporarily considered, one wavelength has the length of about 300 μm. Accordingly, the reflection-type polarization element having the film thickness of about 10 μm has a sufficient transmission capability because the film thickness is 1/30 times smaller than the length of one wavelength. In such a way, the reflection-type polarization element having the film thickness by which a detection signal can be provided with sufficient strength can be used.

The embodiment using the reflection-type polarization element to re-illuminate the emitted and diffused light has been described.

On the other hand, the reflection-type polarization element can be used together with an ordinary reflective member such as a mirror to more effectively utilize the emitted and diffused light. A feature of the reflection-type polarization element which can be disposed in a propagating path of the flux of light and a feature of a reflective member which can reflect all the flux of light independent of its polarization state can go together. For example, in one embodiment, the reflection-type polarization element can be disposed in a propagating path of the flux of light on the surface of a living body (irradiation area), and a reflective member can be placed surrounding it.

EXAMPLES

Examples will be described hereinafter.

Example 1

Figure 2:
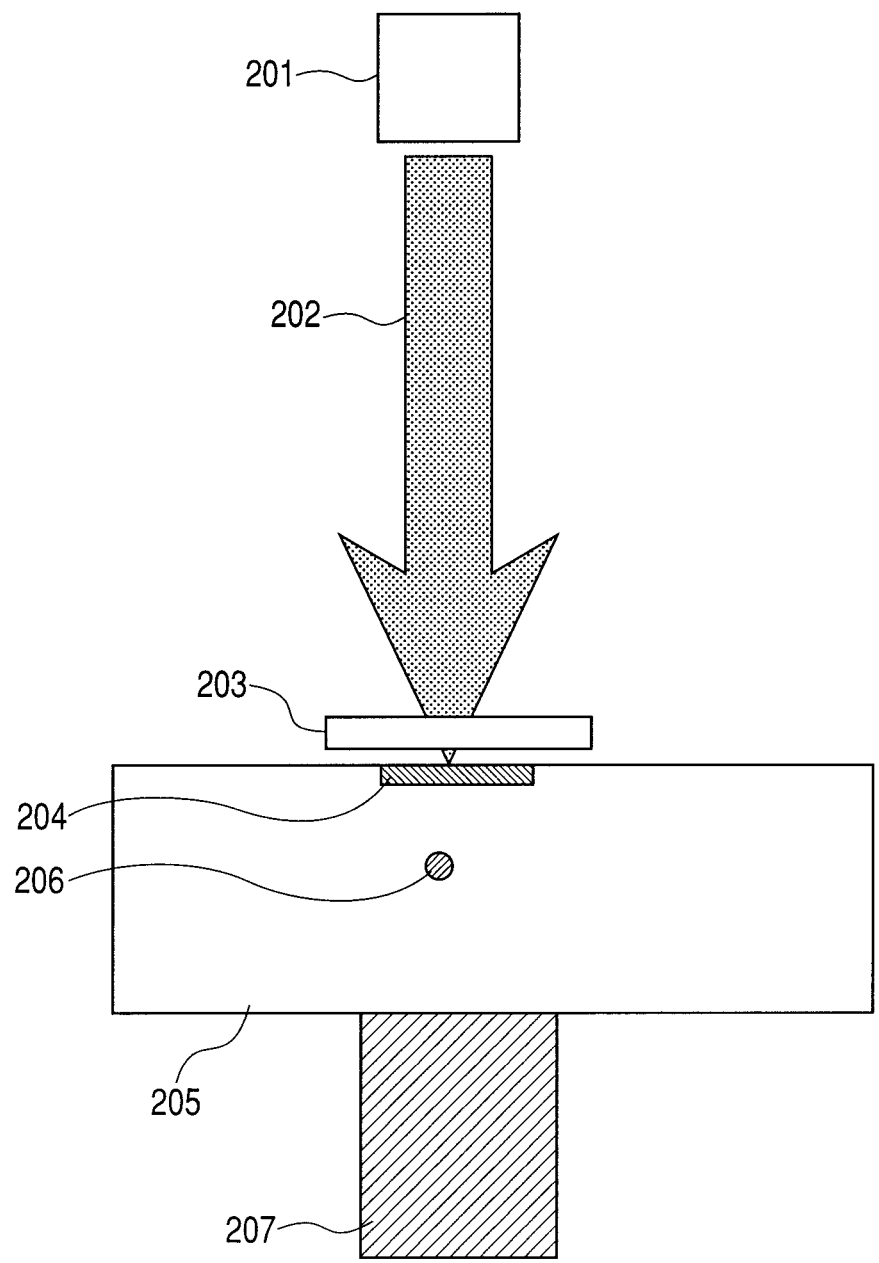
FIG. 2 is a cross-sectional view of an example of a configuration of a bioinformation acquisition apparatus having a reflection-type polarization element according to an Example 1 of the present invention.

Referring to FIG. 2, an example of a configuration of a bioinformation acquisition apparatus having a reflection-type polarization element in an example 1 according to the present invention will be described. A flux of light 202 emitted by a light source 201 is directed to a phantom 205 which is a simulated living body. Here, the flux of light 202 is applied to the surface of the phantom approximately vertically thereto. A reflection-type polarization element 203 is disposed in a propagating path of the flux of light 202 and the surface of the phantom is radiated through the reflection-type polarization element 203.

As the reflection-type polarization element 203, a wire grid polarizer is used here. A polarization state of the flux of light is linear polarization of a p-polarization component and the flux of light 202 passes through the reflection type polarization element 203 without loss of its optical energy. That is, a p-polarization component of the flux of light passing through the reflection-type polarization element is transmitted through and an s-polarization component thereof is reflected.

The reflection-type polarization element 203 is larger than an irradiation area 204 in which the flux of light 202 irradiates the surface of the phantom.

The light source 201 uses the second harmonic wave of a Nd:YAG laser having the wavelength of 532 nm. For the phantom 205, a solution of 10% Intralipid® is used that is diluted with water to have a uniform diffuse factor. A spherical optical absorber 206 is disposed at a position of 2 cm in depth from the irradiation surface inside the Intralipid solution and a photo-acoustical wave signal is measured by an ultrasonic detector 207 disposed on the side opposite to the irradiation surface.

In the case where the reflection-type polarization element 203 described above is disposed, the quantity of the radiated light is increased and the photo-acoustical signal is enhanced, compared with the case without the reflection-type polarization element.

Example 2

Figure 3:
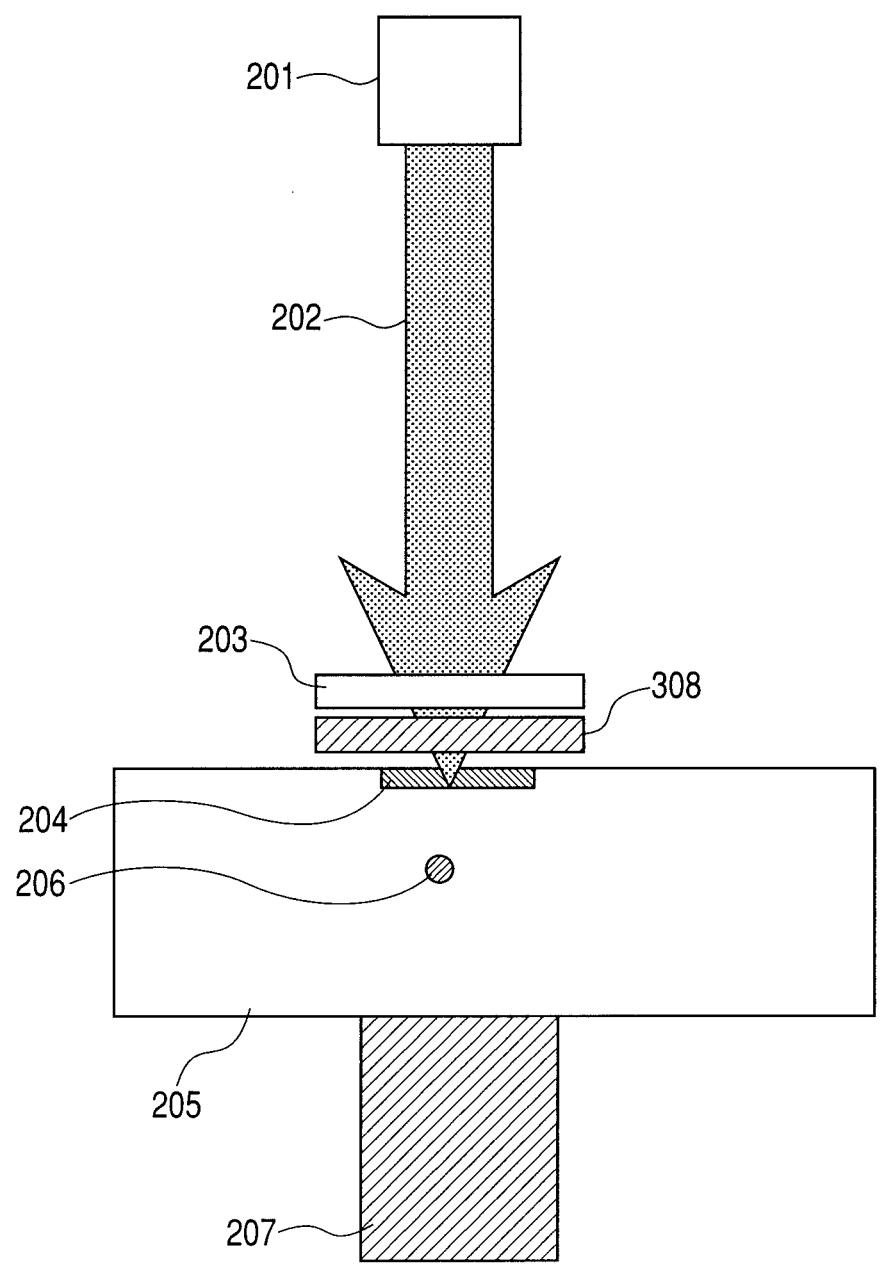
FIG. 3 is a cross-sectional view of an example of a configuration of a bioinformation acquisition apparatus having a reflection-type polarization element according to an Example 2 of the present invention.

Referring to FIG. 3, an example of a configuration of a bioinformation acquisition apparatus having a reflection-type polarization element in an Example 2 according to the present invention will be described. This example basically has a like configuration as Example 1, only differing in that a λ/4 wave plate 308 is inserted between a phantom 205 and a reflection-type polarization element 203. As described in a similar manner in the following examples, overlapping features will be omitted.

In Example 2 configured as described above, the strength of the photo-acoustical signal is intensified, the quantity of the radiated light is increased and the photo-acoustical signal is enhanced, as compared with the case without the reflection-type polarization element 203 and the λ/4 wave plate 308.

Example 3

Figure 4:
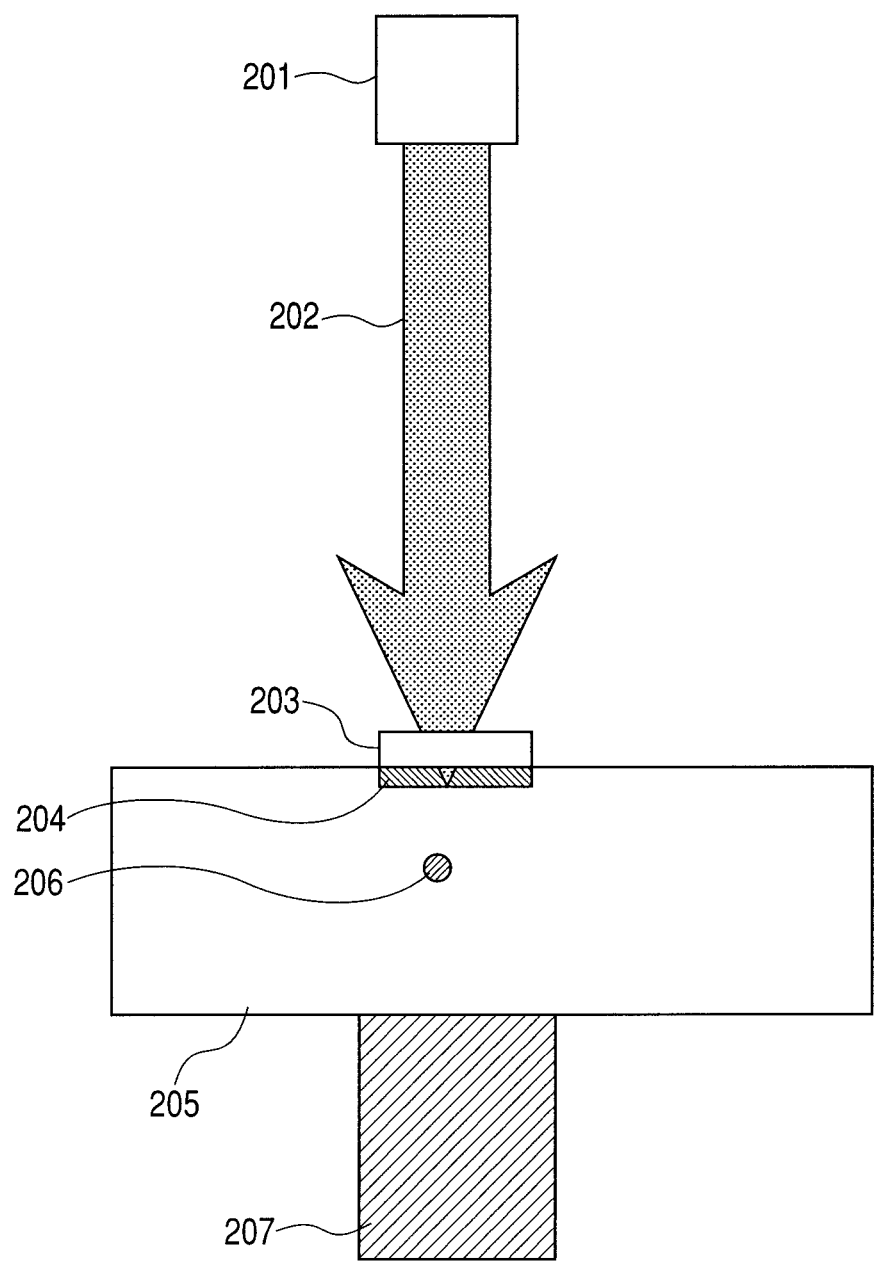
FIG. 4 is a cross-sectional view of an example of a configuration of a bioinformation acquisition apparatus having a reflection-type polarization element according to an Example 3 of the present invention.

Referring to FIG. 4, an example of a configuration of a bioinformation acquisition apparatus having a reflection-type polarization element in an Example 3 according to the present invention will be described. This example basically has a like configuration as Example 1, only differing in that a reflection-type polarization element 203 is positioned in contact with a phantom 205.

When the photo-acoustical signal is detected similarly to Example 1, the quantity of the radiated light is increased and the photo-acoustical signal is enhanced, compared with the case without the reflection-type polarization element. Also, when the reflection type polarization element 203 varied in size is used for measurement, the signal strength is considerably improved at the size thereof equal to or slightly larger than the area of the irradiation area 204.

In this example, the quantity of light applied to the irradiation area can be effectively increased, as compared with the case where the reflection-type polarization element is disposed not contacting ("in non-contact with") the surface of the phantom as in Example 1.

Example 4

Figure 5:
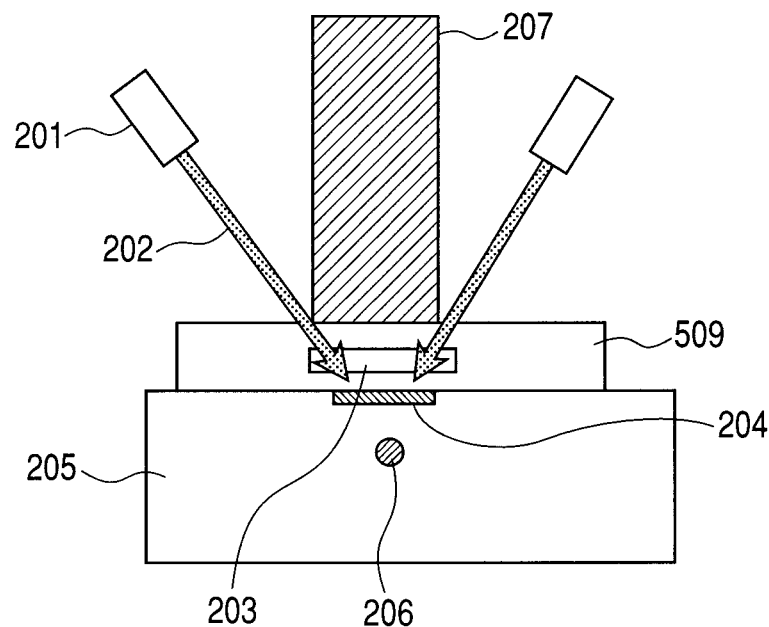
FIG. 5 is a cross-sectional view of an example of a configuration of a bioinformation acquisition apparatus having a -type polarization element according to an Example 4 of the present invention.

Referring to FIG. 5, an example of a configuration of a bioinformation acquisition apparatus having a reflection-type polarization element in an Example 4 according to the present invention will be described. In this example, both an ultrasonic detector 207 and a light source 201 are disposed on the side opposite to a phantom 205. Also, a reflection-type polarization element 203 is disposed in front of the ultrasonic detector 207.

In the case of such an arrangement, it is necessary for the reflection-type polarization element to have features that a flux of light is reflected and an acoustical wave is transmitted through. In this example, the reflection-type polarization element used is such that a dielectric laminated film is coated on a polymethylpentene resin film having a relatively small attenuation of ultrasonic waves. Twenty laminated films are coated and their film thickness is less than 5 μm.

To irradiate a test object 205 behind the ultrasonic detector 207 with a light flux 202, a standoff formed of an acoustically matching material 509 is provided. A light source 501 uses the second harmonic wave of a Nd:YAG laser having the wavelength of 532 nm. For a phantom 505, a solution of 10% Intralipid® is used that is diluted with water to have a uniform diffuse factor. A spherical optical absorber 206 is disposed at a position of 2 cm in depth from the irradiation surface inside the Intralipid® solution.

The acoustical wave is enhanced and the effect can be seen that the quantity of the radiated light is increased because a reflective member is disposed, as compared with the case without the reflection-type polarization element.

Example 5

Figure 6:
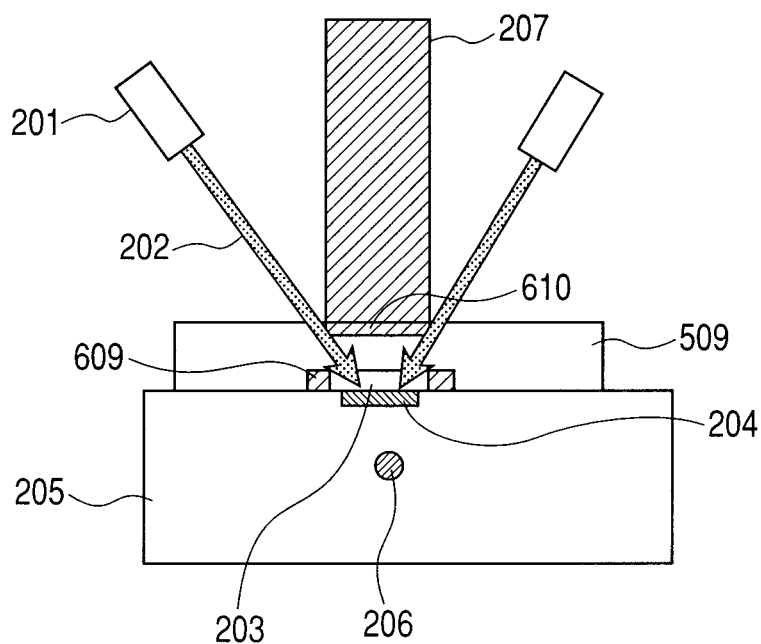
FIG. 6 is a cross-sectional view of an example of a configuration of a bioinformation acquisition apparatus having a reflection-type polarization element according to an Example 5 of the present invention.

Referring to FIG. 6, an example of a configuration of a bioinformation acquisition apparatus having a reflection type polarization element in an Example 5 according to the present invention will be described. This example basically has a like configuration as Example 4, only differing in that a reflective member 609 formed of aluminum surrounding the periphery of a reflection-type polarization element 203 is disposed in an area other than the propagating path of a flux of light 202. Here, the reflection-type polarization element 203 is made as small as possible so as to be disposed only in the propagating path of the flux of light. Also, a reflective film 610 in which an aluminum film having a thickness of 5 μm is deposited on a thin resin film is provided in front of an ultrasonic detector 207.

As compared with Example 4, the strength of the acoustical wave signal is further enhanced and a considerable advantage provided by using both the reflection type-polarization element and the reflective member can be seen.

Example 6

Figure 7:
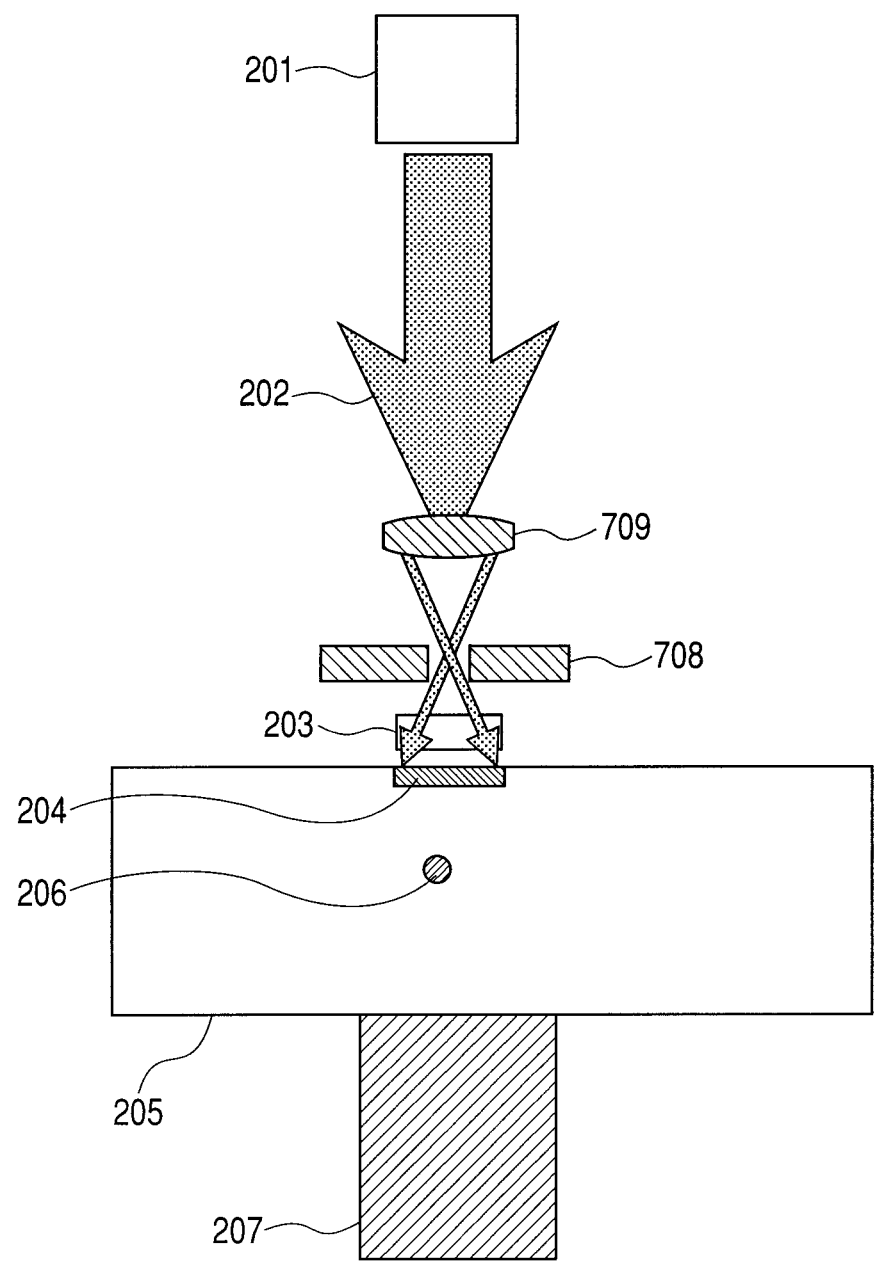
FIG. 7 is a cross-sectional view of an example of a configuration of a bioinformation acquisition apparatus having a reflection-type polarization element according to an Example 6 of the present invention.

Referring to FIG. 7, an example of a configuration of a bioinformation acquisition apparatus having a reflection type polarization element in an Example 6 according to the present invention will be described. This example basically has a like configuration to Example 1, only differing in that there is provided a reflective member 708 with a hole in the central portion so as not to block a propagating path of a flux of light 202. Also, the flux of light 202 is once concentrated at a portion of the hole in the reflective member 708 by using a spherical convex lens 709, passes through a reflection-type polarization element 203 and irradiates a phantom 205. In this example, the reflection-type polarization element 203 is made as small as possible so as to be sized equal to that of the propagating path of the flux of light.

In Example 6, as compared with Example 1, the strength of the acoustical wave signal is further enhanced. The reflection-type polarization element is not limited in installation position and reflects an s-polarization component of emitted and scattered light, and a p-polarization component that has been transmitted through the reflection-type polarization element is reflected by the reflective member 708, whereby optical energy use efficiency is enhanced.

While the present invention has been described with reference to examples, it is to be understood that the invention is not limited to the disclosed examples. The scope of the following claims is to be accorded the broadest interpretation so as to encompass all such modifications and equivalent structures and functions.

This application claims the benefit of Japanese Patent Application No. 2009-253047, filed Nov. 4, 2009, which is hereby incorporated by reference herein in its entirety.

What is claimed is:

1. An information acquisition apparatus comprising:
a light source; and
a polarization element adapted so that at least a part of light from the light source is transmitted through the polarization element and is directed to an object, wherein
the polarization element is disposed so that light that is reflected by the object is reflected by the polarization element and directed to the object.

2. The information acquisition apparatus according to claim 1, wherein the polarization element transmits a linear polarization component of the light from the light source.

3. The information acquisition apparatus according to claim 1, wherein the size of the polarization element is equal to or larger than a region that is irradiated with the transmitted light.

4. The information acquisition apparatus according to claim 1, wherein the object is irradiated with the transmitted light from an approximately vertical direction.

5. The information acquisition apparatus according to claim 1, further comprising a λ/4 wave plate provided between the polarization element and the object.

6. The information acquisition apparatus according to claim 1, wherein the polarization element is disposed in contact with the surface of the object.

7. The information acquisition apparatus according to claim 1, further comprising a detector, wherein
an acoustical wave is generated by irradiation of the object with the light from the light source,
the detector comprises an acoustical wave-detector for detecting the acoustical wave,
the polarization element comprises a member that transmits the acoustical wave, and
the polarization element is disposed between the detector and the irradiation area.

8. The information acquisition apparatus according to claim 1, further comprising a reflective member disposed near the polarization element arranged such that the reflective member does not block a path of a flux of light from the light source to the surface of the object.

9. The information acquisition apparatus according to claim 8, wherein the reflective member is a mirror.

10. The information acquisition apparatus according to claim 1, wherein the polarization element reflects a linear polarization component that is different from the transmitted linear polarization component.

11. The information acquisition apparatus according to claim 1, wherein the reflection type polarization element covers a region that is irradiated with the transmitted light.

12. The information acquisition apparatus according to claim 1, further comprising a light detector that detects light propagated and diffused inside the object.

13. The information acquisition apparatus according to claim 1, further comprising a light detector that detects modulated light resulting from modulation of the light by an ultrasonic wave.

14. The information acquisition apparatus according to claim 1, further comprising a detector that detects X-ray phase variation in the object.

* * * * *